United States Patent
Yang et al.

(10) Patent No.: US 6,290,970 B1
(45) Date of Patent: Sep. 18, 2001

(54) TRANSFERRIN RECEPTOR PROTEIN OF MORAXELLA

(75) Inventors: Yan-Ping Yang, Willowdale; Lisa E. Myers, Guelph; Robin E. Harkness; Michel H. Klein, both of Willowdale, all of (CA)

(73) Assignee: Aventis Pasteur Limited, Toronto (CA)

( * ) Notice: Subject to any disclaimer, the term of this patent is extended or adjusted under 35 U.S.C. 154(b) by 0 days.

(21) Appl. No.: 08/540,753

(22) Filed: Oct. 11, 1995

(51) Int. Cl.$^7$ .......................... A61K 39/02; A61K 38/00; C07K 14/00; C07K 17/00
(52) U.S. Cl. ...................... 424/251.1; 530/350; 530/412; 424/190.1; 424/250.1; 424/184.1; 424/234.1; 514/2
(58) Field of Search ........................ 530/350; 424/190.1, 424/251.1, 234.1, 184.1, 250.1; 514/2

(56) References Cited

U.S. PATENT DOCUMENTS

| | | |
|---|---|---|
| 5,552,146 | * 9/1996 | Hansen et al. . |
| 5,618,541 | * 4/1997 | Quentin-Millet . |
| 5,922,841 | * 7/1999 | Loosmore et al. . |
| 5,928,650 | * 7/1999 | Quentin-Millet et al. . |
| 5,977,337 | * 11/1999 | Loosmore et al. . |
| 6,015,688 | * 1/2000 | Loosmore et al. . |
| 6,028,049 | * 2/2000 | Jacobs et al. . |
| 6,090,576 | * 7/2000 | Myers et al. . |
| 6,190,668 | * 2/2001 | Yang et al. . |

FOREIGN PATENT DOCUMENTS

| | | |
|---|---|---|
| WO 90/03184 | 4/1990 | (WO) . |
| 9012591 | * 11/1990 | (WO) . |
| WO 90/12591 | 11/1990 | (WO) . |
| WO 91/06287 | 5/1991 | (WO) . |
| 9116072 | * 10/1991 | (WO) . |
| 9303761 | * 3/1993 | (WO) . |
| WO 93/03761 | 3/1993 | (WO) . |

OTHER PUBLICATIONS

Lazar et al. Mol. Cell Biology 8(3): 1247–52 3/88.*
Burgess et al. J. Cell Biology 111: 2129–39 11/90.*
Sethi et al. Infec. Immunity 63(4): 1516–20 4/95.*
Bluestone, C.D., Clin. Infect. Dis. 14 (Suppl): S197–S203 (1992).
Van Hare, G.F., P.A. Shurin, C.D. Marchant, N.A. Cartelli, C.E. Johnson, D. Fulton, S. Carlin, and C.H. Kim. Acute otitis media caused by Branhamella catarrhalis: biology and therapy. Rev. Infect. Dis. 9:16–27.
Chapman, A.J., D.M. Musher, S. Jonsson, J.E. Clarridge, and R.J. Wallace. 1985. Development of bactericidal antibody during Branhamella catarrhalis infection. J. Infect. Dis. 151:878–882.
Hagar, H., A. Verghese, S. Alvarez, and S.L. Berk. 1987. Branhamella catarrhalis respiratory infections. Rev. Infect. Dis. 9:1140–1149.
McLeod, D.T., F. Ahmad, M.J. Croughan, and M.A. Calder. 1986. Bronchopulmonary infection due to M. catarrhalis. Clinical features and therapeutic response. Drugs 31(Suppl.3):109–112.
Ninane, G., J. Joly, and M. Kraytman. 1978. Bronchopulmonary infection due to Branhamella catarrhalis 11 cases assessed by transtracheal puncture. Br.Med.Jr. 1:276–278.
Srinivasan, G., M.J. Raff, W.C. Templeton, S.J. Givens, R.C. Graves, and J.C. Mel. 1981. Branhamella catarrhalis pneumonia. Report of two–cases and review of the literature. Am.Rev. Respir. Dis. 123:553–555.
West, M., S.L. Berk, and J.K. Smith. 1982. Branhamella catarrhalis pneumonia. South.Med. J. 75:1021–1023.
Brorson, J.–E., A. Axelsson, and S.E. Holm. 1976. Studies on Branhamella catarrhalis (Neisseria catarrhalis) with special reference to maxillary sinusitis. Scan. J. Infect. Dis. 8:151–155.
Evans, F.O., Jr., J.B. Sydnor, W.E.C. Moore, G.R. Moore, J.L. Manwaring, A.H. Brill, R.T. Jackson, S. Hanna, J.S. Skaar, L.V. Holdeman, G.S. Fitz–Hugh, M.A. Sande, and J.M. Gwaltney, Jr. 1975. Sinusitis of the maxillary anstrum. N.Engl.J.Med. 293:735–739.
Tinkelman, D.G., and H.J. Silk. 1989. Clinical and bacteriologic features of chronic sinusitis in children. Am.J.Dis. Child. 143:938–942.
Nicotra, B., M. Rivera, J.I. Luman, and R.J. Wallace. 1986.Branhamella catarrhalis as a lower respiratory tract pathogen in patients with chronic lung disease. Arch. Intern. Med. 146: 890–893.
Wald, E.R., C. Byers, N.Guerra, M.Casselbrant, and D. Beste. 1989. Subacute sinusitis in children. J.Pediatr. 115:28–32.
Wald, E.R., G.J. Milmoe, A. Bowen, J.Ledesma–Medina, N. Salamon, and C.D.Bluestone. 1981. Acute maxillary sinusitis in children. N.Engl.J.Med. 304:749–754.
Christensen, J.J., and B. Bruun. 1985. Bacteraemia caused by a beta–lactamase producing strain of Branhamella catarrhalis. Acta.Pathol. Microbiol. Immunol. Scand. Sect.B 93:273–275.
Craig, D.B., and P.A. Wehrle. 1983. Branhamella catarrhalis septic arthritis. J. Rheumatol. 10:985–986.
Gray, L.D., R.E. Van Scoy, J.P. Anhalt, and P.K.W. Yu. 1989. Wound infection caused by Branhamella catarrhalis. J.Clin. Microbiol. 27:818–820.
Guthrie, R., K. Bakenhaster, R.Nelson, and R. Woskobnick. 1988. Branhamella catarrhalis sepsis: a case report and review of the literature. J.Infect.Dis. 158:9097–908.

(List continued on next page.)

Primary Examiner—Nita Minnifield
(74) Attorney, Agent, or Firm—Sim & McBurney

(57) ABSTRACT

An isolated and purified non-denatured transferrin receptor protein of a Moraxella strain, particularly M. catarrhalis, has an apparent molecular mass of about 80 to about 90 kDa, as determined by SDS-PAGE. The transferrin receptor protein or a fragment analog thereof is useful in diagnostic applications and immunogenic compositions, particularly for in vivo administration to a host to confer protection against disease caused by a strain of Moraxella.

7 Claims, 8 Drawing Sheets

OTHER PUBLICATIONS

Hiroshi, S., E.J. Anaissie, N.Khardori, and G.P. Bodey. 1988. *Branhamella catarrhalis* septicemia in patients with leukemia. Cancer 61:2315–2317.

O'Neill, J.H., and P.W. Mathieson. 1987. Meningitis due to *Branhamella catarrhalis*. Aust. N.Z. J. Med. 17:241–242.

Morgan, M.G., McKenzie, H, Enright, M.C., Bain, M. and Emmanuel, F.X.S. (1992) Use of molecular methods to characterize *Moraxella catarrhalis* strains in a suspected outbreak of nosocomial infection. Eur. J. Clin. Microbiol. Infect. Dis. 11, 305–312.

Wallace, M.R., Oldfield, B.C., 1990, *Arch. Intern. Med.* 150: 1332–1334.

Otto, B.R., Verweij-van, Vught A.M.J.J. MacLaren, D.M. 1992, *Crit. Rev. Microbiol.* 18: 217–233.

Schryvers, A.B. and Morris, L.J. 1988 Identification and Characterization of the transferrin receptor from *Neisseria meningitidis*. Mol. Microbiol. 2:281–288.

Lee, B.C., Schryvers, A.B. Specificity of the lactoferrin and transferrin receptors in *Neisseria gonorrhoeae*. Mol. Microbiol. 1988; 2–827–9.

Schryvers, A.B. Characterization of the human transferrin and lactoferrin receptors in *Haemophilus influenzae*. Mol. Microbiol. 1988; 2:467–72.

Schryvers, A.B. and Lee, B.C. (1988) Comparative analysis of the transferrin and lactoferrin binding proteins in the family *Neisseriaceae*.Can. J. Microbiol. 35, 409–415.

Schryvers, A.B. and Gonzalez, G.C.1989. Comparison of the abilities of different protein sources of iron to enchance *Neisseria meningitidis* infection in mice. Infect. Immun. 57:2425–2429.

Yu, R. and Schryvers, A.B., 1993. The interaction between human transferrin and transferrin binding protein 2 from *Moraxella* (Branhamella) *catarrhalis* differs from that of other human pathogens. Microbiol. Pathogenesis, 15:433–445.

Campagnari, A.A., Shanks, K.L., Dyer D.W. 1994, Infect. Immun. 62: 4909–4914.

Lockhoff, O. Glycolipids as Immunomodulators: Synthesis and Properties. 1991. Chem. Int. Ed. Engl. 30:1611–1620.

Nixon–George et al (1990), J. Immunology, 144:4798–4802.

Sarwar, J., Campagnari, A.A., Kirkham, C. and Murphy, T.F. (1992). Characterization of an antigenically conserved heat–modifiable major outer membrane protein of *Branhamella catarrhalis*, Infect. Immun. 60, 804–809.

Lugtenberg, B., Meijers, J., Peters, R., van der Hoek, P. and van Alphen, L. (1975). Electrophoretic resolution of the major outer membrane proteins of *Escherichia coli* into four bands. FEBS Lett. 58, 254–258.

Towbin H., Staehelin, T., Gordon, J. 1979, *Proc. Natl. Acad. Sci.* 76: 4350–4354.

Murphy, Timothy F. and Bartos, Linda C. Surface–Exposed and Antigenically Conserrved Determinants of Outer Membrane Proteins of *Branhamella catarrhalis* Infection and Immunity, Oct. 1989, p. 2938–2941 vol. 57, No. 10.

Bhushan, Reva; Craigie, Robert and Murphy, Timoth F. Molecular Cloning and Characterisztation of outer Membrane Protein of *Moraxella* (Branhamella) *catarrhalis*. Journal of Bacteriology, Nov. 1994, p. 6636–6643, vol. 176, No. 21.

Klingman, Karin L. and Murphy, Timothy F. Purification and Characterization of a High–Molecular–Weight Outer Membrane Protein of *Moraxella* (Branhamella) *catarrhalis*. Infectiion and Immunity, Apr. 1994, p. 1150–1155, vol. 62, No. 4.

Beaulieu, Danielle; Scriver, Shelley; Bergeron, Michel G.; Low, Donald E.; Parr, Thomas R. Jr.; Patterson, Jan Evans; Matlow, Anne and Roy, Paul H. Epidemiological Typing of *Moraxella catarhalis* by using DNA Probes Journal of Clinical Microbiology, Mar. 1993, p. 736–739, vol. 31, No. 3.

Myers, Lisa E.; Yang, Yan–Ping; Du, Run–Pan; Wang, Qijun; Harkness, Robin E.; Schryvers, Anthony B.; Klien, Michel H. and Loosmore, Shema M. The Transferrin Binding Protein of *Moraxella catarrhalis* Elicits Bactericidal Antibodies and Is a Potential Vaccine Antigen. Infection and Immunity, Sep. 1998, p. 4183–4192, vol. 66 No. 9.

Sethi, Sanjay; Hill, Susan L. and Murphy, Timothy F. Serum Antibodies to Outer Membrane Proteins (OMPs) of *Moraxella* (Branhamella) *catarrhalis* in Patients with Bronchiectasis: Identification of OMP B1 as an Important Antigen. Infection and Immunity. Apr. 1995, p. 1516–1520. vol. 63 No. 4.

Helminen, Merja E.; Maciver, Isobel; Latimer, Jo L.; Cope, Leslie D.; McCracken, George H. Jr. and Hansen, Eric J. A Major Outer Membrane Protein of *Moraxella catarrhalis* Is a Target for Antibodies That Enhance Pulmonary Clearance of the Panthogen in an Animal Model. Infection and Immunity,. May 1993, p. 2003–2010, vol. 61, No. 5.

Aebi, Christoph; Cope, Leslie D.; Latimer Jo. L.; Thomas, Sharon E.; Slaughter Clive A.; McCracken, George H. Jr. and Hansen, Eric J. Mapping of a Protective Epitope of the CopB Outer Membrane Protein of *Moraxella catarrhalis*. Infection and Immunity, Feb. 1998, p. 540–548, vol. 66, No. 2.

Murphy, Timothy F. Studies of the Outer Membrane Proteins of *Branhamella catarrhalis* The American Journal of Medicine, May 14, 1990, vol. 88 (suppl 5A), pp. 41S to 45S.

\* cited by examiner

1. Lysate of *M. catarrhalis* strain 4223
2. TfR2 extract (TfR2-1)
3. Run-through of DEAE (TfR2-2)
4. Run-through of SE-cellulose/ D529 (TfR2-3)
5. Run-through of HTP (Protein B)
6. HTP bound fraction (TfR2)
7. Affinity purified TfR2

1. Affinity purified TfR2

2. TfR2 preparation

3. Protein B preparation

IMMUNO-BLOT

TRANSFERRIN RECEPTOR PROTEIN OF MORAXELLA

FIELD OF THE INVENTION

The present invention relates to the field of immunology and is particularly concerned with transferrin receptor protein from Moraxella, methods of production, and uses thereof.

BACKGROUND OF THE INVENTION

Otitis media is the most common illness of early childhood with approximately 80% of all children suffering at least one bout of otitis media before the age of three (ref. 1—Throughout this application, various references are referred to in parenthesis to more fully describe the state of the art to which this invention pertains. Full bibliographic information for each citation is found at the end of the specification, immediately preceding the claims. The disclosures of these references are hereby incorporated by reference into the present disclosure). Chronic otitis media can lead to hearing, speech and cognitive impairment in children. It is caused by bacterial infection with Streptococcus pneumoniae (approximately 50%), non-typable Haemophilus influenzae (approximately 30%) and Moraxella (Branhamella) catarrhalis (approximately 20%). In the United States alone, treatment of otitis media costs between one and two billion dollars per year for antibiotics and surgical procedures, such as tonsillectomies, adenoidectomies and insertion of tympanostomy tubes. Because otitis media occurs at a time in life when language skills are developing at a rapid pace, developmental disabilities specifically related to learning and auditory perception have been documented in youngsters with frequent otitis media.

M. catarrhalis mainly colonizes the respiratory tract and is predominantly a mucosal pathogen. Studies using cultures of middle ear fluid obtained by tympanocentesis have shown that M. catarrhalis causes approximately 20% of cases of otitis media (ref. 2).

Long regarded as an opportunistic pathogen, B. catarrhalis is now recognized to cause a variety of potentially debilitating human diseases as a result of localized or, more rarely, systemic infection.

M. catarrhalis is an important cause of lower respiratory tract infections in adults, particularly in the setting of chronic bronchitis and emphysema (refs. 3, 4, 5, 6, 7, 8 and 9). M. catarrhalis also causes sinusitis in children and adults (refs. 10. 11, 12, 13 and 14) and occasionally causes invasive disease (refs. 15, 16, 17, 18, 19 and 20). In the hospital setting, M. catarrhalis has been suspected in outbreaks of nosocomial infection (ref. 21).

The incidence of otitis media caused by M. catarrhalis is increasing. As ways of preventing otitis media caused by pneumococcus and non-typeable H. influenzae are developed, the relative importance of M. catarrhalis as a cause of otitis media can be expected to further increase. Also antibiotic resistance is becoming common in clinical isolates of M. catarrhalis (ref 22). Thus, prior to 1970 no β-lactamase producing M. catarrhalis strains had been reported, but since the mid seventies, β-lactamase expressing strains have been detected with ever increasing frequency among isolates. Recent surveys suggest that 75% of clinical isolates produce β-lactamase.

Iron-restriction is a general host defence mechanism against microbial pathogens, however, it is not necessarily growth rate-limiting for all pathogens (ref. 23). A number of bacterial species including Neisseria meningitidis (ref. 24), N. gonorrhoeae (ref. 25) and Haemophilus influenzae (ref. 26), expresses two outer membrane proteins which specifically bind human transferrin (refs. 27, 28). The expression of these proteins is regulated by the amount of iron in the growth environment. Unlike the receptors of other bacterial species, the M. catarrhalis receptors have a preferred affinity for iron-laden (i.e., ferri-) transferrin (ref. 29). The two M. catarrhalis transferrin receptors (TfR) have molecular masses of 115 kDa (TfR1) and about 80 to 90 kDA (TfR2) (ref. 27).

The outer membrane protein OMP B2 (refs. 30, 31) has a molecular mass similar to that of TfR2, and it has been reported that the expression of OMP B2 is iron-regulated (ref. 32).

Yu and Schryvers (ref. 29) describe a method for purification of the transferrin receptor proteins TfR1 and TfR2 from M. catarrhalis by selective elution from a transferrin-sepharose affinity column using the denaturing agent guanidine HCl.

In this method of the preparative isolation of receptor proteins, a suspension of iron-deficient crude M. catarrhalis membranes was solubilized by the addition of EDTA to 20 mM and Sarkosyl to 0.75% and then the mixture was centrifuged for 15 minutes at 20,000×g to remove debris. Twenty ml of $Fe_2hTf$-Sepharose (i.e. an iron-saturated form of human transferrin) was added to the supernatant and then incubated with mixing at room temperature for 45 minutes. The mixture was applied to a column and after removing the binding solution, the resin was washed with an additional 250 ml of 50 mM Tris-HCl, 1 M NaCl, 20 mM EDTA, 0.75% Sarkosyl, pH 8 buffer containing 250 mM guanidine HCl. The TfR2 protein was eluted using a buffer (lacking Sarkosyl) containing 1.5 M guanidine-HCl and subsequently the TfR1 protein was eluted by the application of a buffer containing 4 M guanidine-HCl. The fractions were dialysed against 50 mM Tris HCl, pH 8 over a 24 hour period.

In a further modification of this procedure, apohTf-Sepharose was mixed with the solubilized membrane preparation in order to bind TfR1 and then the treated solubilized membrane preparation was exposed to $Fe_2hTf$-Sepharose to bind the remaining TfR2. The affinity resins were subsequently washed and the receptor proteins eluted as described above M. catarrhalis infection may lead to serious disease. It would be advantageous to provide non-denatured transferrin receptor protein from M. catarrhalis for use as antigens in immunogenic preparations including vaccines, carriers for other antigens and immunogens and the generation of diagnostic reagents.

SUMMARY OF THE INVENTION

The present invention is directed towards the provision of purified and isolated transferrin receptor protein of Moraxella catarrhalis and other Moraxella strains, having an apparent molecular mass of about 80 to 90 kDa.

In accordance with one aspect of the invention, there is provided an isolated and purified, non-denatured transferrin receptor protein of a Moraxella strain having an apparent molecular mass of about 80 to about 90 kDa, as determined by sodium dodecyl sulphate polyacrylamide gel electrophoresis (SDS-PAGE), or a fragment or an analog thereof (TfR2). The transferrin receptor protein may be substantially in its native conformation (so as to have substantially retained the characteristic immunogenicity of the transferrin receptor protein in the Moraxella strain) and may be isolated from a *M. catarrhalis* strain, such as from *M. catarrhalis* 4223, 5191 or 135. Such isolated and purified transferrin receptor protein of apparent molecular mass of about 80 to about 90 kDa is substantially free from non-80 to 90 kDa Moraxella proteins, particularly the OMP B2 protein and the transferrin receptor protein having an apparent molecular mass of about 105 kDa of the Moraxella strains, phospholipids and lipopolysaccharide of Moraxella. The about 80 to about 90 kDa transferrin receptor protein is at least about 70 wt % pure, preferably at least about 90 wt % pure, and may be in the form of an aqueous solution thereof.

The present invention also provides an immunogenic composition comprising an immunoeffective amount of an active component, which may be the transferrin receptor protein or fragment or analog thereof, provided herein along with a pharmaceutically acceptable carrier therefor. The immunogenic composition may be formulated as a vaccine for in vivo administration to a host to confer protection against diseases caused by a strain of Moraxella, particularly *M. catarrhalis*. The immunogenic composition may be formulated as a microparticle capsule, ISCOM or liposome preparation. The immunogenic composition may be used in combination with a targeting molecule for delivery to specific cells of the immune system or to mucosal surfaces. Some targeting molecules include strain B12 and fragments of bacterial toxins, as described in WO 92/17167 (Biotech Australia Pty. Ltd.), and monoclonal antibodies, as described in U.S. Pat. No. 5,194,254 (Barber et al). The immunogenic compositions of the invention (including vaccines) may further comprise at least one other immunogenic or immunostimulating material and the immunostimulating material may be at least one adjuvant. Suitable adjuvants for use in the present invention include, (but are not limited to) aluminum phosphate, aluminum hydroxide, QS21, Quil A, derivatives and components thereof, calcium phosphate, calcium hydroxide, zinc hydroxide, a glycolipid analog, an octadecyl ester of an amino acid, a muramyl dipeptide, polyphosphazene and a lipoprotein. Advantageous combinations of adjuvants are described in copending U.S. patent application Ser. No. 08/261,194 filed Jun. 16, 1994, assigned to the assignee hereof and the disclosure of which is incorporated herein by reference. The invention further includes an antibody specific for the transferrin receptor protein provided herein producible by immunizing a host with an immunogenic composition as provided herein.

The immunogenic compositions provided herein may be formulated to comprise at least one additional immunogen, which may comprise or be derived from a paramyxovirus, Chlamydia, polio, hepatitis B, diphtheria toxoid, tetanus toxoid, influenza, haemophilus, pertussis, pneumococcus, mycobacteria and hepatitis A.

In a further aspect of the invention, there is provided a method of generating an immune response in a host, comprising administering thereto an immuno-effective amount of the immunogenic composition as provided herein. The immune response may be a humoral or a cell-mediated immune response. Hosts in which protection against disease may be conferred include primates including humans.

The present invention provides, in an additional aspect thereof, a method of producing a vaccine comprising administering the immunogenic composition provided herein to a test host to determine an amount and a frequency of administration of the transferrin receptor protein to confer protection against disease caused by a strain of Moraxella and formulating the transferrin receptor protein in a form suitable for administration to a treated host in accordance with said determined amount and frequency of administration. The treated host may be a human.

A further aspect of the invention provides a method of determining the presence in a sample of antibodies specifically reactive with a transferrin receptor protein of a strain of Moraxella having a molecular mass of about 80 to about 90 kDa, comprising the steps of:
  (a) contacting the sample with the transferrin receptor protein as provided herein to produce complexes comprising the transferrin receptor protein and any said antibodies present in the sample specifically reactive therewith; and
  (b) determining production of the complexes.

In a further aspect of the invention, there is provided a method of determining the presence in a sample of a transferrin receptor protein of a strain of Moraxella having a molecular mass of about 80 to about 90 kDa, in a sample comprising the steps of:
  (a) immunizing a subject with the immunogenic composition as provided herein, to produce antibodies specific for the transferrin receptor protein;
  (b) contacting the sample with the antibodies to produce complexes comprising any outer membrane protein present in the sample and said outer membrane protein specific antibodies; and
  (c) determining production of the complexes.

The transferrin receptor protein may be part of a *Moraxella catarrhalis* strain.

A further aspect of the invention provides a diagnostic kit for determining the presence of antibodies in a sample specifically reactive with the transferrin receptor protein of a strain of Moraxella having a molecular mass of about 80 to about 90 kDa, comprising:
  (a) the transferrin receptor protein as provided herein;
  (b) means for contacting the transferrin receptor protein with the sample to produce complexes comprising the transferrin receptor protein and any said antibodies present in the sample; and
  (c) means for determining production of the complexes, The invention also provides a diagnostic kit for detecting the presence, in a sample, of a transferrin receptor protein of a strain of Moraxella having a molecular mass of about 80 to about 90 kDa comprising:
  (a) an antibody specific for the about 80 to about 90 kDa transferrin receptor protein as provided herein;
  (b) means for contacting the antibody with the sample to produce a complex comprising the transferrin receptor protein and transferrin receptor protein-specific antibody; and
  (c) means for determining production of the complex.

The present invention provides, in a further aspect, a method of producing a vaccine, comprising administering the immunogenic composition provided herein to a test host to determine an amount and a frequency of administration thereof to confer protection against disease caused by a Moraxella strain that produces a transferrin receptor protein having an apparent molecular mass of about 80 to about 90 kDa, as determined by SDS-PAGE or a protein capable of inducing antibodies in a test host specifically reactive with the transferrin protein; and formulating the immunogenic composition in a form suitable for administration to a treated host, including a human host, in accordance with the determined amount and frequency of administration.

In an additional aspect of the invention, there is provided a method of producing monoclonal antibodies specific for a transferrin receptor protein of a Moraxella strain having an apparent molecular mass of about 80 to about 90 kDa, comprising:

(a) administrating the transferrin receptor protein provided herein to at least one mouse to produce at least one immunized mouse, (b) removing B-lymphocytes from the at least one immunized mouse;

(c) fusing the B-lymphocytes from the at least one immunized mouse with myeloma cells, thereby producing hybridomas;

(d) cloning the hybridomas;

(e) selecting clones which produce anti-transferrin receptor protein antibody;

(f) culturing the anti-transferrin receptor protein antibody-producing clones; and then (g) isolating anti-transferrin receptor protein antibodies from the cultures.

In a further aspect of the invention, there is provided a method of producing an isolated and purified non-denatured transferrin receptor protein of a strain of Moraxella, such as *M. catarrhalis* having a molecular mass of about 80 to about 90 kDa, comprising the steps of:

(a) providing a cell mass of the Moraxella strain;

(b) selectively extracting aqueous soluble proteins from the cell mass to provide a first supernatant and a first pellet;

(c) separating the first supernatant from the first pellet;

(d) selectively solubilizing at least a transferrin receptor protein having a molecular mass of about 80 to 90 kDa from the first pellet to provide a second supernatant and a second pellet;

(e) separating the second supernatant from the second pellet; and (f) purifying transferrin receptor protein having a molecular mass of about 80 to about 90 kDa in the second supernatant substantially free from other Moraxella proteins solubilized from the first pellet in the selective solubilization step.

The aqueous soluble proteins may be selectively extracted from the cell mass by contacting the cell mass with a buffered aqueous solution, which may comprise about 50 mM to about 1 M Tris-HCl at a pH of about 7 to about 8.5, sonication of the cell mass to disrupt the same, and centrifugation to form the first pellet and the first supernatant. The selective solubilization step may be effected by contacting the first pellet at least once with a buffered aqueous solution, which may be about 20 mM to about 1 M Tris-HCl, comprising a detergent, which may be about 0.2 to about 2 wt. % of TRITON X-100 (Trademark for non-ionic detergent which is octadecylphenol (ethylene glycol) 10), and a solubilizing agent, which may be about 2 to about 20 mM of EDTA, sonication of the first pellet to disrupt the same and centrifugation to form the second pellet and the second supernatant. Such contacting, sonication and centrifugation steps may be effected at least twice and supernatant from each such step is then pooled to provide the second supernatant.

The purification step may be effected by multiple chromatographic column operations, which may include:

(a) a first chromatographic operation on a first chromatography column, which may be a DEAE-Sephacel column through which the transferrin receptor selectively flows and on which contaminating proteins bind, such as by use of a buffer comprising about 10 mM to about 1 M Tris-HCl at a pH of about 7 to about 8.5, (b) a second chromatographic operation on a second chromatography column comprising a cation-exchange matrix, such as SE-Cellulose/D529, through which the transferrin receptor selectively flows and on which contaminating proteins bind, such as by use of a buffer comprising about 10 mM to about 1 M Tris-HCl at a pH of about 7 to about 8.5, (c) a third chromatographic operation on a third chromatography column, such as hydroxyapatite, on 5 which the transferrin receptor protein is selectively bound in preference to OMP B2 protein, such as by loading the column at a pH of about 7 to about 8.5, and (d) eluting the transferrin receptor protein from 10 the third chromatography column, such as by using a buffer solution having a pH of about 7 to about 8.5 containing about 100 to about 250 mM $KH_2PO_4$.

The preparation procedure provided herein results in the isolation of the transferrin receptor protein in a purified form and in a nondenatured form.

In this application, the term "a transferrin receptor protein (Tfr2) of a Moraxella strain having an apparent molecular mass of about 80 to about 90 kDa" is used to define a family of transferrin receptor proteins of *M. catarrhalis* having molecular mass of between about 80 and about 90 kDa and includes proteins having variations in their amino acid sequences including those naturally occurring in various strains of Moraxella. In this application, a first protein is a "functional analog" of a second protein if the first protein is immunologically related to and/or has the same function as the second protein. The functional analog may be, for example, a fragment of the protein or a substitution, addition or deletion mutant thereof.

Advantages of the present invention include:

a method for isolating purified transferrin receptor protein having an apparent molecular mass of about 80 to about 90 kDa from a Moraxella strain that produces the transferrin receptor protein, including *Moraxella catarrhalis*;

an isolated and purified non-denatured transferrin receptor protein having an apparent molecular mass of about 80 to about 90 kDa and isolatable from a Moraxella strain; and diagnostic kits and immunological reagents for specific identification of Moraxella and hosts infected thereby.

BRIEF DESCRIPTION OF THE FIGURES

The present invention will be further understood from the following description with reference to the FIGURES, in which.

GENERAL DESCRIPTION OF INVENTION

The present invention provides novel techniques which can be employed for preparing purified transferrin receptor protein Tfr1 from *M. Catarrhalis*. Any *M. Catarrhalis* strain that produces Tfr2 may be conveniently used to provide the isolated and purified Tfr2 as provided herein. Such strains are generally available from clinical sources and from bacterial culture collections. Appropriate strains of *M. catarrhalis* may include *M. catarrhalis* 5191, 135 and 4223.

Referring to FIG. 1, there is illustrated a flow diagram of a method for purifying a transferrin protein from *M. catarrhalis* having an apparent molecular mass of about 80 to about 90 kDa, as determined by SDS-PAGE according to one embodiment of the invention. The various operations described below may be effected at ambient temperatures, generally about 4° to about 30° C. Whole cells are contacted with an aqueous buffer medium, which may contain about 10 mM to about 1 M Tris-HCl at pH about 7 to about 8.5 and disrupted by sonication to produce, following centrifugation, a first supernatant (S1) and a first pellet (PPT1). The supernatant (S1) contains a substantial proportion of the soluble protein from the cell pellet and is discarded. The remaining pellet (PPT1) is selectively detergent extracted to remove any residual soluble proteins and to solubilize membrane proteins, including the TfR2 protein, from the pellet. Such selective extraction may be effected in any convenient manner. One such procedure may involve multiple detergent extractions of the pellet. In particular, a first detergent extraction may be effected using Triton X-100 and EDTA followed by centrifugation to form a second pellet (PPT2) and a second supernatant (S2), which is retained. Following separation of the second supernatant (S2), the residual pellet PPT2 is again detergent extracted using Triton X-100 and EDTA, followed by centrifugation. The resulting third supernatant (S3), following separation from the residual third pellet (PPT3), which is discarded, is combined with the second supernatant (S2) from the first extraction to provide pooled supernatants (TfR2-1). Such Triton X-100 extractions may be effected using a solution of concentration about 0.2 to about 2 wt % Triton X-100 and about 2 to about 20 mM EDTA under buffer conditions, such as a pH about 7 to about 8.5, using about 10 mM to about 1 M Tris.

Figure 1A:
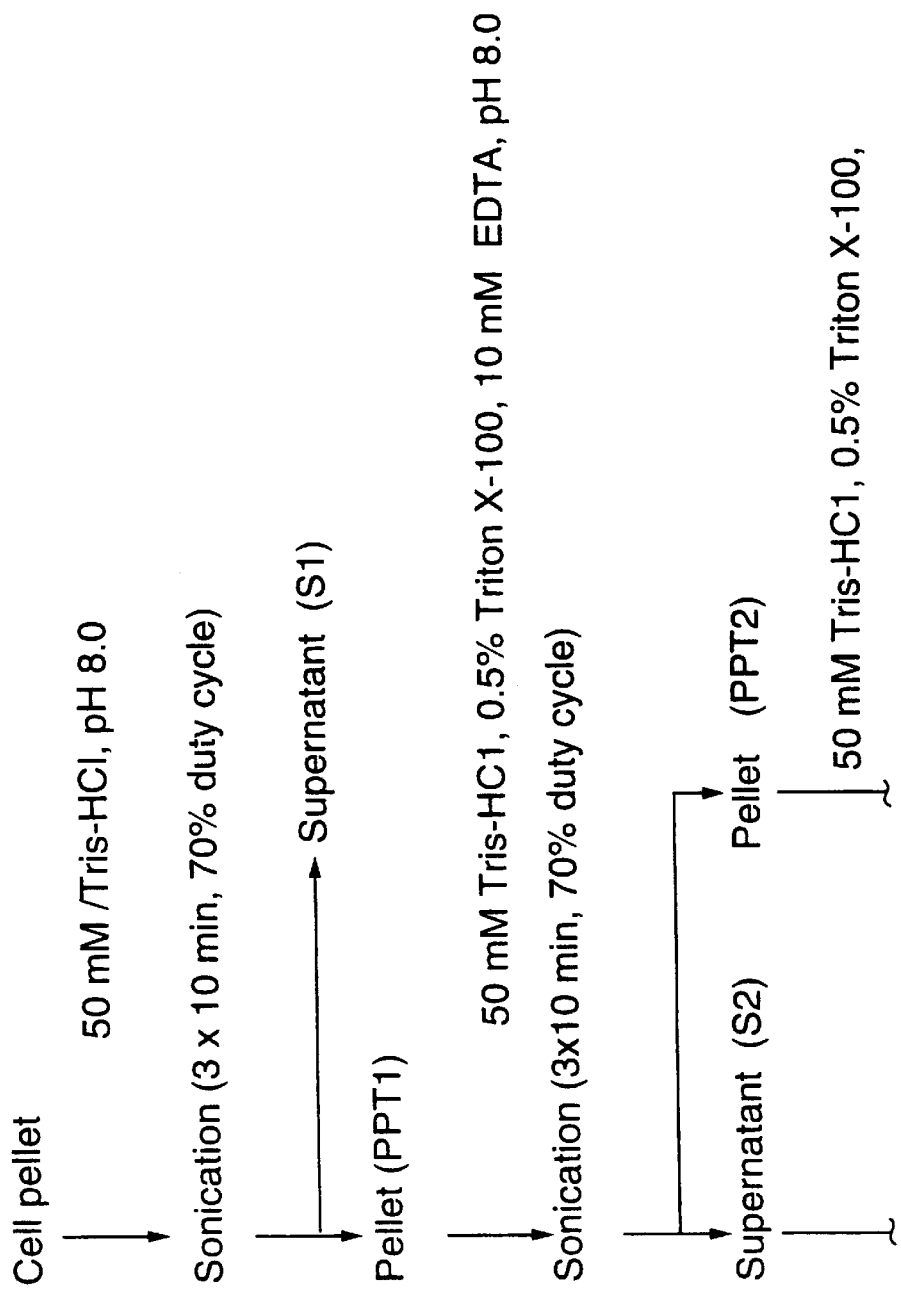
FIGS. 1A, 1B, 1C and 1D are a flow diagram of a method for purifying transferrin receptor protein from *Moraxella catarrhalis*, according to one embodiment of the invention.
Figure 1B:
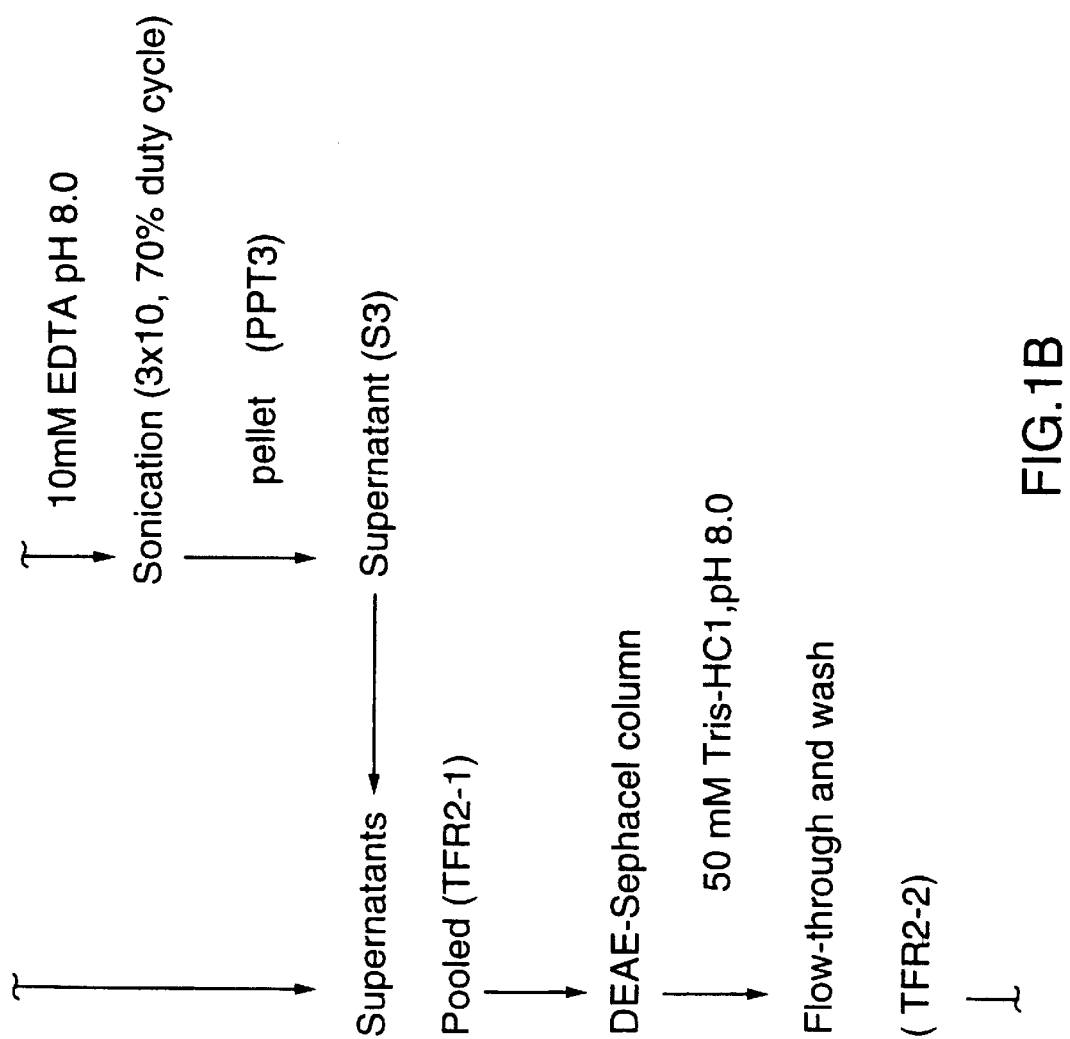
Figure 1C:
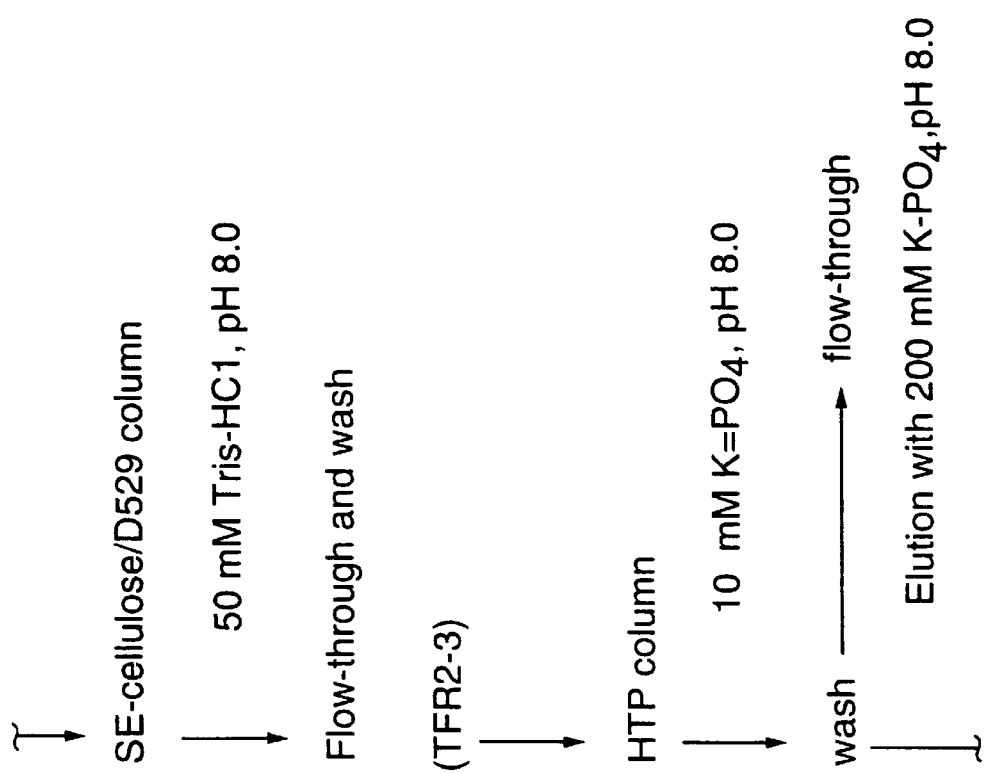
Figure 1D:
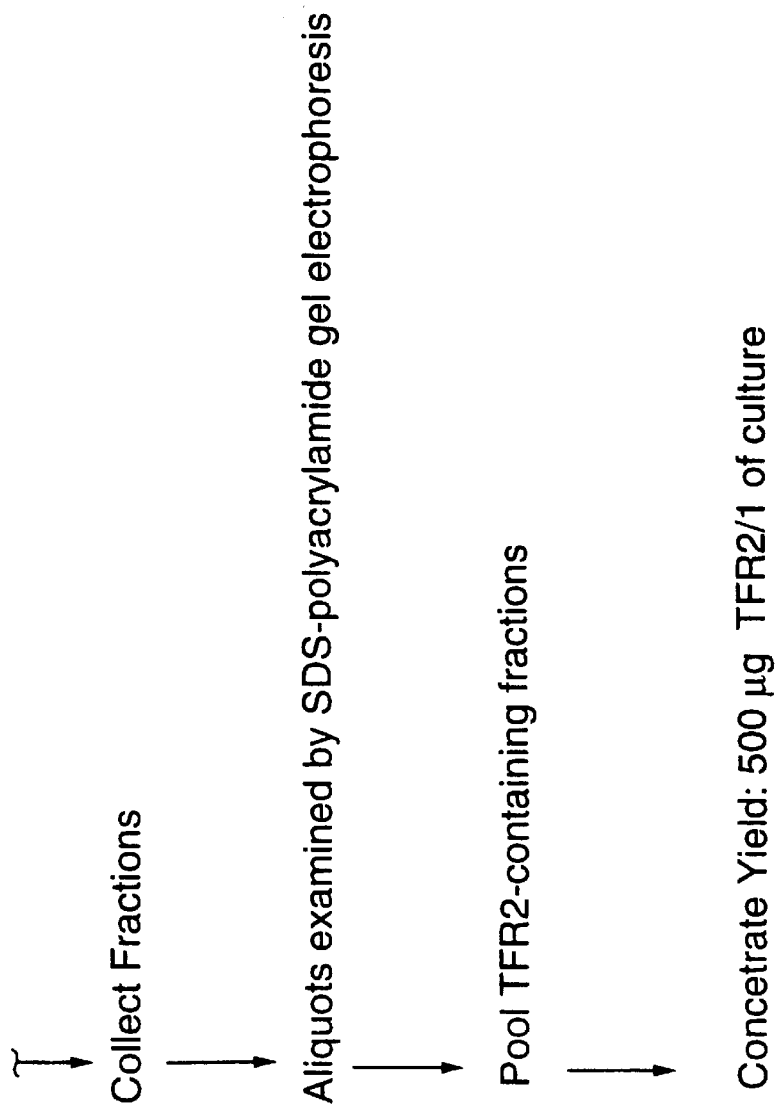
Figure 2:
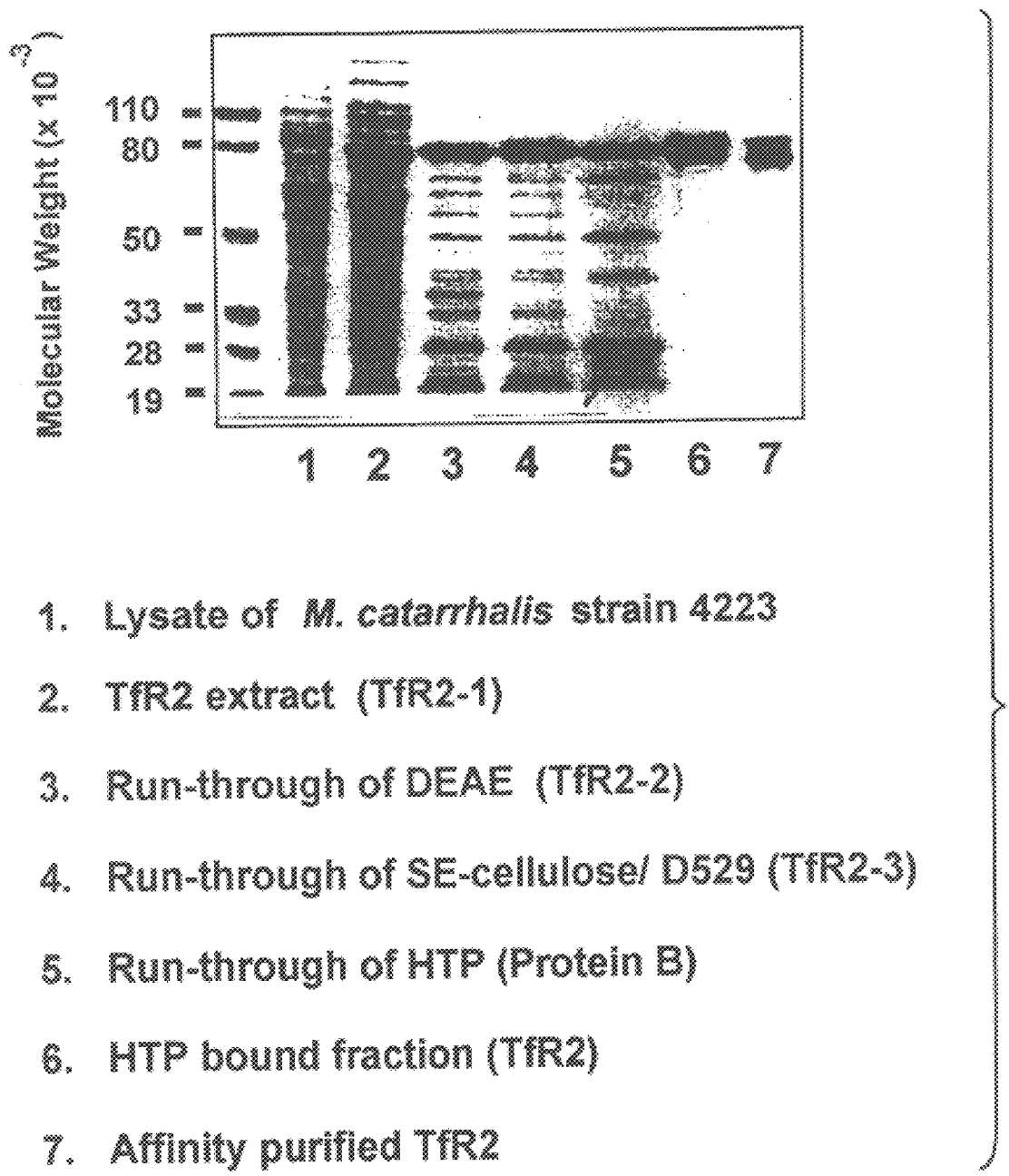
FIG. 2 shows the ability of purified transferrin receptor to bind human transferrin.

The pooled supernatants (TfR2-1) contain the TfR2 rotein, as well as contaminating *M. catarrhalis* proteins, including the OMP B2 protein which has the same approximate molecular mass (see Lanes 3 and 5, FIG. 2). The pooled supernatants (TfR2-1) are processed to remove such impurities in a series of column chromatography operations.

In a first such column chromatography operation, the pooled supernatants (TfR2-1) may be applied to a DEAE-Sephacel column or other suitable column, suitably buffered, such as with about 10 mM to about 1 M Tris-HCl at a pH of about 7 to about 8.5, to permit the TfR2 protein to pass through the column, while impurities are bound to the column. The DEAE-Sephacel column may be washed before further processing of the flow through.

The flow through and wash from the DEAE-Sephacel column (TfR2-2) then may be applied to a cation-exchange column, for example, SE-cellulose/D529 or S-Sepharose, suitably buffered, such as with about 10 mM to about 1 M Tris-HCl at pH about 7 to about 8.5, to permit TfR2 protein to pass through the column, while impurities are bound to the columns. The cation-exchange column may be washed before further processing of the flow-through (see lane 4, FIG. 2).

The flow-through and wash from the cation-exchange column (TfR2-3), which still contains the OMP B2 protein, as well as small quantities of residual proteinaceous contaminants, then may be applied to a hydroxyapatite column under such buffer conditions that the TfR2 protein binds to the column in preference to the OMP B2 protein and other contaminating proteins, which pass through the column. Such conditions may be provided using about 5 to about 50 mM potassium phosphate buffer at pH about 6 to about 8.5. The flow-through contains the contaminating proteins (see lane 5, FIG. 2).

Following repeated washing with the buffer to remove column-retained contaminants, the TfR2 protein then is eluted from the hydroxyapatite column using a suitable buffer, such as about 150 to about 250 mM potassium phosphate buffer solution at pH about 7 to about 8.5. The eluted fractions are collected, aliquots analyzed by SDS-PAGE and TfR2-containing fractions pooled. The pooled fractions may be concentrated to provide a TfR2 protein-containing solution (see lane 6, FIG. 2). By this procedure, there is provided an aqueous solution of an isolated and purified non-denatured TfR2 protein. The aqueous TfR2 solution may be provided in any convenient concentration consistent with the intended use of the material, generally about 100 to about 200 µg/ml.

Referring to FIG. 2, there is shown an analysis of the purity of transferrin receptor protein by SDS-PAGE analysis, purified by the method described herein as typified by that schematically shown in FIG. 1. In FIG. 2, Lane 1 shows the *M. catarrhalis* cell lysate. Lane 2 shows the pooled supernatants (TfR2-1). Lane 3 shows the run-through fraction following DEAE-Sephacel column chromatography (TfR2-2) and Lane 4 shows the run-through fraction of SE-cellulose/D529 column chromatography (TfR2-3). Lane 5 shows the flow-through fraction of HTP and contains the OMP B2 protein. Lane 6 shows the HTP bound fraction containing TfR2. Lane 7 shows transferrin receptor protein TfR2 isolated by affinity chromatography essentially as described in ref. 29. The method for purification of TfR2 protein as provided herein produces at least a 70% pure TfR2 protein preparation. The illustrated preparation in Lane 6 in FIG. 2 is at least 95% pure, as determined by densitometry scanning.

Figure 3A:
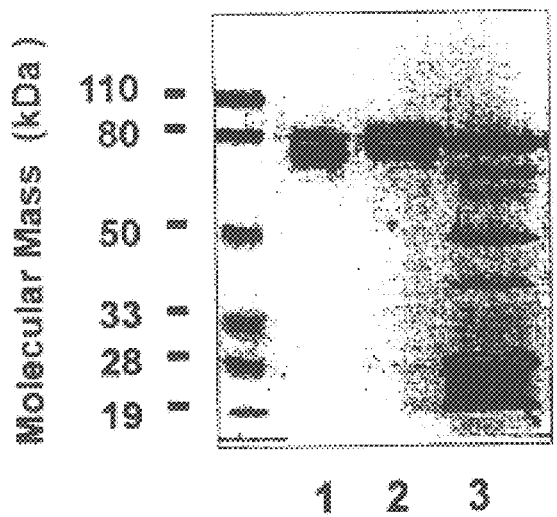
FIGS. 3A and 3B shows an analysis by SDS-PAGE of isolated and purified transferrin receptor protein having an apparent molecular mass of about 80 to about 90 kDa.
Figure 3B:
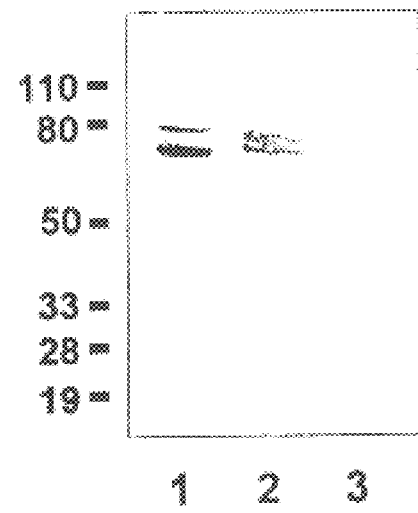

Referring to FIG. 3, there is illustrated the ability of purified TfR2 of *M. catarrhalis* as provided herein to specifically bind human transferrin. Proteins were separated by SDS-PAGE and in vitro transferrin binding assessed essentially as described in ref. 27. Lane 1 contains TfR2 of *M. catarrhalis* isolated by affinity chromatography essentially as described in ref. 29. Lane 2 contains TfR2 from *M. catarrhalis* purified as described herein. Lane 3 contains *M. catarrhalis* OMPB2 protein. As can be seen from FIG. 3, the transferrin binding protein preparations specifically bind transferrin. These results confirm the isolation of TfR2 from *M. catarrhalis* by the method provided herein.

To be useful as a component of immunogenic compositions (including vaccines) and as an antigen in diagnostic embodiments, the transferrin receptor protein purified as described herein should advantageously be capable of generating antibodies that recognize or neutralize *M. catarrhalis* strains, including a plurality thereof.

Figure 4A:
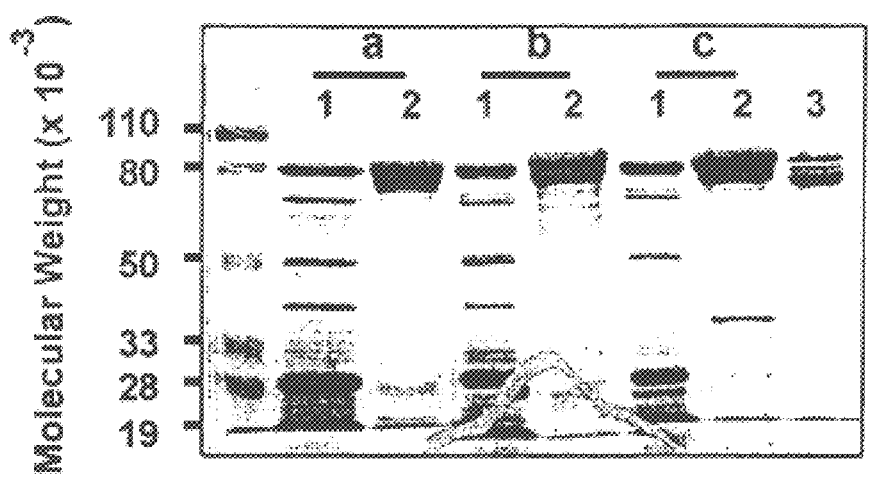
FIGS. 4A, 4B and 4C show an immunoblot analysis of purified transferrin receptor protein.
Figure 4B:
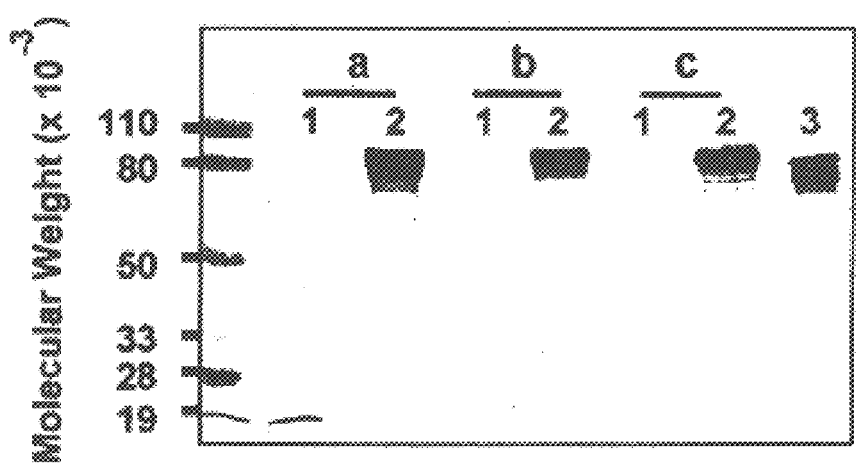
Figure 4C:
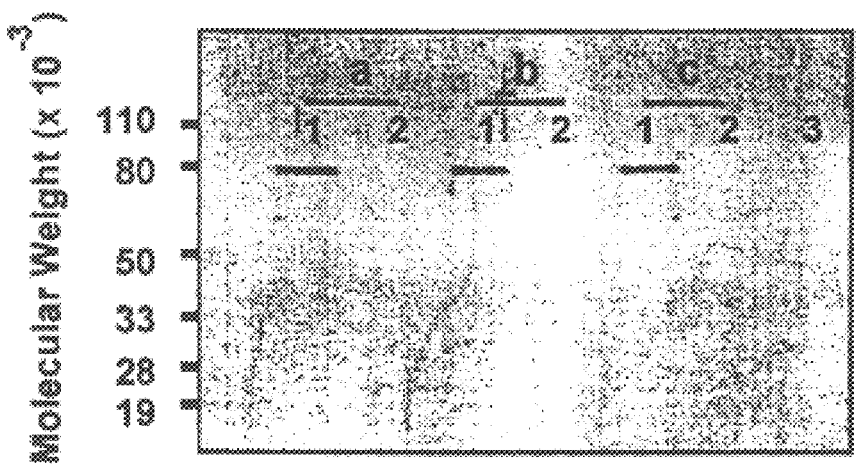

Referring to FIGS. 4(*a*), 4(*b*) and 4(*c*), there is shown an immunoblot analysis of TfR2 as provided herein and shows the specific separation of TfR2 from OMP B2 protein. In each of the FIGURES, sample 1 contains OMP B2 protein and sample 2 contains TfR2 protein. The *M. catarrhalis* strains were a: strain 5191; b: strain 135; and c: strain 4223. Samples were separated by SDS-PAGE. Sample 3 was purified TfR2. FIG. 4(*a*) shows a Coomassie blue stained gel. FIG. 4(b) shows an immunoblot using an anti-TfR2 antiserum. FIG. 4(c) shows an immunoblot using an anti-OMP B2 antiserum. The results of FIG. 4 confirm the specific purification of transferrin receptor protein TfR2 from M. catarrhalis by the method provided herein and particularly substantially free from OMBP2 protein.

Figure 5A:
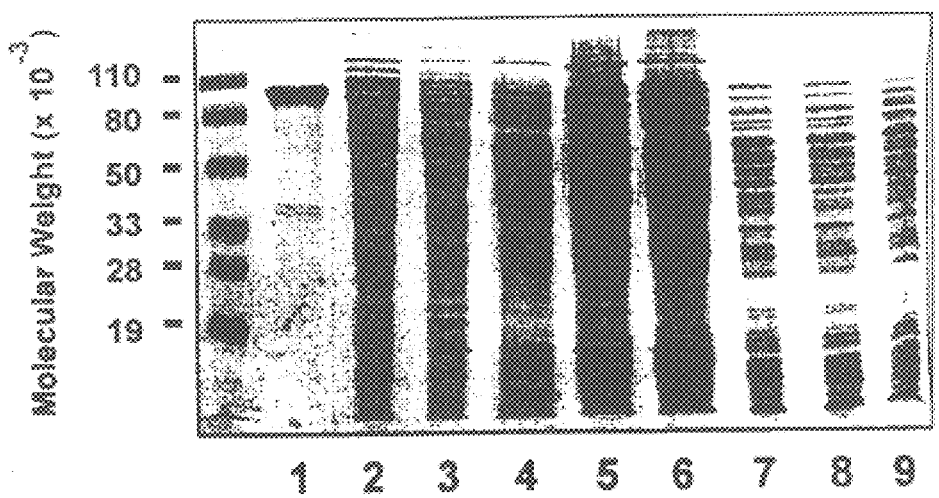
FIGS. 5A and 5B are immunoblots to demonstrate the ability of guinea pig anti-Tfr antisera produced by immunization with isolated and purified transferrin receptor protein to specifically distinguish between *M. catarrhalis* and other bacterial pathogens that cause otitis media.
Figure 5B:
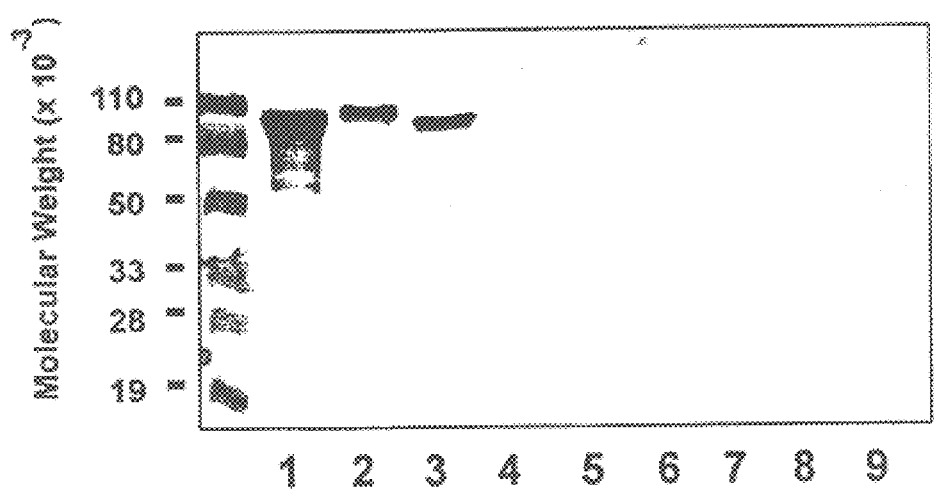

Referring to FIG. 5(b), there is illustrated an immunoblot showing the ability of guinea pigs anti-TfR antisera produced by immunizing guinea pigs with purified TfR protein as provided herein to recognize TfR2 protein from M. catarrhalis isolated from a variety of sources. The samples tested were as follows:

| Lane | M. catarrhalis | Source |
| --- | --- | --- |
| 1 | Purified TfR2 | M. catarrhalis 4223 |
| 2 | 56 | Middle ear fluid |
| 3 | 4223 | Middle ear fluid |

In one embodiment of the present invention, the isolated and purified TfR2 protein as provided herein is useful for generating antibodies that can be used to specifically distinguish M. catarrhalis from other bacterial pathogens that cause otitis media. Thus referring to FIGS. 5(a) and 5(b), there is illustrated an SDS-PAGE and an immunoblot respectively showing the specific reactivity of guinea pig anti-TfR2 antisera produced by immunizing guinea pigs with TfR2 protein as provided herein. The samples analyzed were as follows:

| Lane | Bacterium | Source |
| --- | --- | --- |
| 1 | TfR2 protein | M. catarrhalis 4223 |
| 2 | M. catarrhalis 56 | Middle ear fluid |
| 3 | M. catarrhalis 4223 | Middle ear fluid |
| 4 | H. influenzae strain 12 | |
| 5 | H. influenzae strain 30 | Otitis media isolate |
| 6 | H. influenzae LCOC 1 | Otitis media isolate |
| 7 | S. pneumoniae | ATCC 6303 |
| 8 | S. pneumoniae | ATCC 6304 |
| 9 | S. pneumoniae | ATCC 6314 |

The results shown in FIG. 5(b) clearly show the usefulness of TfR2-specific antisera as provided herein to distinguish between bacterial pathogens that produce diseases with similar clinical symptoms.

Results shown in Table 1 below illustrate the ability of guinea pig anti-TfR2 antisera produced by immunization with TfR2 protein as provided herein, to kill M. catarrhalis. The results show that antisera produced by immunization with TfR2 protein isolated from strain 4223 were bactericidal against a homologous non-clumping M. catarrhalis strain RH408 derived from strain 4223. The ability of the isolated and purified TfR2 protein as provided herein to generate bactericidal antibodies is in vivo evidence of utility of the TfR2 protein as provided herein as a vaccine to protect against diseases caused by M. catarrhalis.

Thus, in accordance with another aspect of the present invention, there is provided a vaccine against Moraxella or other bacterial pathogens that produce TfR2 protein or produce a protein capable of inducing antibodies that specifically recognize TfR2, comprising an immunogenically-effective amount of TfR2 protein as provided herein and a physiologically-acceptable carrier therefor. The TfR2 protein provided herein also may be used as a carrier protein for hapten, polysaccharides or peptides to make a conjugate vaccine against antigenic determinants unrelated to TfR2.

The TfR2 protein provided herein is useful as a diagnostic reagent, as an antigen or for the generation of anti-TfR2 antibodies, antigen for vaccination against the diseases caused by species of Moraxella.

In additional embodiments of the present invention, the TfR2 protein as provided herein may be used as a carrier molecule to prepare chimeric molecules and conjugate vaccines (including glycoconjugates) against pathogenic bacteria, including encapsulated bacteria. Thus, for example, glycoconjugates of the present invention may be used to confer protection against disease and infection caused by any bacteria having polysaccharide antigens including lipooligosaccharides (LOS) and PRP. Such bacterial pathogens may include, for example, Haemophilus influenzae, Streptococcus pneumoniae, Escherichia coli, Neisseria meningitidis, Salmonella typhi, Streptococcus mutants, Cryptococcus neoformans, Klebsiella, Staphylococcus aureus and Pseudomonas aeruginosa. Particular antigens which can be conjugated to TfR2 protein and methods to achieve such conjugations are described in published PCT application WO 94/12641, assigned to the assignee hereof and the disclosure of which is hereby incorporated by reference thereto.

In another embodiment, the carrier function of TfR2 protein may be used, for example, to induce immunity toward abnormal polysaccharides of tumor cells, or to produce anti-tumor antibodies that can be conjugated to chemotherapeutic or bioactive agents.

The present invention extends to the TfR2 protein for use as a pharmaceutical substance, particularly as an active ingredient in a vaccine against diseases caused by infection of a strain of Moraxella.

In a further aspect, the invention provides the use of the TfR2 protein for the preparation of a medicament for immunization against diseases caused by infection with a strain of Moraxella.

It is clearly apparent to one skilled in the art, that the various embodiments of the present invention have many applications in the fields of vaccination, diagnosis, treatment of Moraxella infections and the generation of immunological reagents. A further non-limiting discussion of such uses is further presented below.

1. Vaccine Preparation and Use

Immunogenic compositions, suitable to be used as vaccines, may be prepared from immunogenic transferrin receptor, proteins or analogs as disclosed herein. Preferably, the antigenic material is extensively dialyzed to remove undesired small molecular weight molecules and/or myophilized for more ready formulation into a desired vehicle. The immunogenic composition elicits an immune response which produces antibodies, including anti-transferrin receptor antibodies and antibodies that are opsonizing or bactericidal. Should the vaccinated subject be challenged by Moraxella or other bacteria that produce a transferrin receptor, the antibodies bind to the transferrin receptor and thereby prevent access of the bacteria to an iron source which is required for viability. Furthermore, opsonizing or bactericidal anti-TfR antibodies may also provide protection by alternative mechanisms.

Immunogenic compositions including vaccines may be prepared as injectables, as liquid solutions or emulsions. The transferrin receptor protein may be mixed with pharmaceutically acceptable excipients which are compatible therewith. Such excipients may include, water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by injection subcutaneously or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Such suppositories may be formed from mixtures containing the active ingredient(s) in the range of about 0.5 to about 10%, preferably about 1 to 2%. Oral formulations may include normally employed incipients such as, for example, pharmaceutical grades of saccharine, cellulose and magnesium carbonate. These compositions can take the form of solutions, suspensions, tablets, pills, capsules, sustained release formulations or powders and contain about 1 to 95% of the transferrin receptor protein, preferably about 20 to about 75%.

The immunogenic preparations and vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies, the degree of protection desired and if needed, to produce a cell-mediated immune response. Precise amounts of active ingredient required to be administered depend on the judgment of the practitioner. However, suitable dosage ranges are readily determinable by one skilled in the art and may be of the order of micrograms of the transferrin receptor protein per vaccination. Suitable regimes for initial administration and booster doses are also variable, but may include an initial administration followed by subsequent administrations. The dosage may also depend on the route of administration and will vary according to the size of the host.

The concentration of the transferrin receptor protein in an immunogenic composition according to the invention is in general about 1 to 95%. A vaccine which contains antigenic material of only one pathogen is a monovalent vaccine. Vaccines which contain antigenic material of several pathogens are combined vaccines and also belong to the present invention. Such combined vaccines contain, for example, material from various pathogens or from various strains of the same pathogen, or from combinations of various pathogens.

Immunogenicity can be significantly improved if the antigens are co-administered with adjuvants, commonly used as 0.05 to 0.1 percent solution in phosphate-buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and a HBsAg vaccine has been adjuvanted with alum. While the usefulness of alum is well established for some applications, it has limitations. For example, alum is ineffective for influenza vaccination and inconsistently elicits a cell mediated immune response. The antibodies elicited by alum-adjuvanted antigens are mainly of the IgG1 isotype in the mouse, which may not be optimal for protection by some vaccinal agents.

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are often emulsified in adjuvants. Many adjuvants are toxic, inducing granulomas, acute and chronic inflammations (Freund's complete adjuvant, FCA), cytolysis (saponins and Pluronic polymers) and pyrogenicity, arthritis and anterior uveitis (LPS and MDP). Although FCA is an excellent adjuvant and widely used in research, it is not licensed for use in human or veterinary vaccines because of its toxicity.

Desirable characteristics of ideal adjuvants include:
(1) lack of toxicity;
(2) ability to stimulate a long-lasting immune response;
(3) simplicity of manufacture and stability in long-term storage;
(4) ability to elicit both CMI and HIR to antigens administered by various routes, if required;
(5) synergy with other adjuvants;
(6) capability of selectively interacting with populations of antigen presenting cells (APC);
(7) ability to specifically elicit appropriate $T_H1$ or $T_H2$ cell-specific immune responses; and
(8) ability to selectively increase appropriate antibody isotype levels (for example, IgA) against antigens.

U.S. Pat. No. 4,855,283 granted to Lockhoff et al on Aug. 8, 1989 which is incorporated herein by reference thereto teaches glycolipid analogues including N-glycosylamides, N-glycosylureas and N-glycosylcarbamates, each of which is substituted in the sugar residue by an amino acid, as immuno-modulators or adjuvants. Thus, Lockhoff et al. (U.S. Pat. No. 4,855,283 and ref. 33) reported that N-glycolipid analogs displaying structural similarities to the naturally-occurring glycolipids, such as glycosphingolipids and glycoglycerolipids, are capable of eliciting strong immune responses in both herpes simplex virus vaccine and pseudorabies virus vaccine. Some glycolipids have been synthesized from long chain-alkylamines and fatty acids that are linked directly with the sugars through the anomeric carbon atom, to mimic the functions of the naturally occurring lipid residues.

U.S. Pat. No. 4,258,029 granted to Moloney, assigned to the assignee hereof and incorporated herein by reference thereto, teaches that octadecyl tyrosine hydrochloride (OTH) functioned as an adjuvant when complexed with tetanus toxoid and formalin inactivated type I, II and III poliomyelitis virus vaccine. Also, Nixon-George et al. (ref. 34), reported that octadecyl esters of aromatic amino acids complexed with a recombinant hepatitis B surface antigen, enhanced the host immune responses against hepatitis B virus.

2. Immunoassays

The transferrin receptor protein of the present invention is useful as an immunogen for the generation of anti-transferrin receptor protein antibodies, as an antigen in immunoassays including enzyme-linked immunosorbent assays (ELISA), RIAs and other non-enzyme linked antibody binding assays or procedures known in the art for the detection of anti-bacterial, anti-Moraxella, and anti-TfR antibodies. In ELISA assays, the transferrin receptor protein is immobilized onto a selected surface, for example, a surface capable of binding proteins such as the wells of a polystyrene microtiter plate. After washing to remove incompletely adsorbed transferrin receptor protein, a non-specific protein such as a solution of bovine serum albumin (BSA) that is known to be antigenically neutral with regard to the test sample may be bound to the selected surface. This allows for blocking of nonspecific adsorption sites on the immobilizing surface and thus reduces the background caused by nonspecific bindings of antisera onto the surface.

The immobilizing surface is then contacted with a sample, such as clinical or biological materials, to be tested in a manner conducive to immune complex (antigen/antibody) formation. This may include diluting the sample with diluents, such as solutions of BSA, bovine gamma globulin (BGG) and/or phosphate buffered saline (PBS)/Tween. The sample is then allowed to incubate for from 2 to 4 hours, at temperatures such as of the order of about 25 to 37° C. Following incubation, the sample-contacted surface is washed to remove non-immunocomplexed material. The washing procedure may include washing with a solution, such as PBS/Tween or a borate buffer. Following formation of specific immunocomplexes between the test sample and the bound transferrin receptor protein, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity such as an enzymatic activity that will generate, for example, a colour development upon incubating with an appropriate chromogenic substrate. Quantification may then be achieved by measuring the degree of colour generation using, for example, a spectrophotometer.

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitations.

Methods of molecular genetics, protein biochemistry, and immunology used but not explicitly described in this disclosure and these Examples are amply reported in the scientific literature and are well within the ability of those skilled in the art.

Example 1

This Example illustrates the growth of M. catarrhalis.

The M. catarrhalis strains used were 135, 4223 (ref. 35), 5191 (ref. 35) (all middle ear isolates), ATCC 25240, Q8 (expectorate isolate) and RH408.

To provide cells for isolation of TfR2, M. catarrhalis strains were routinely maintained on chocolate agar plates (BBL).

M. catarrhalis strain 4223 was inoculated into 20 mL of brain heart infusion (BHI) broth. The culture was incubated overnight with aeration at 37° C. For growth under iron-restricted conditions, one mL of the overnight-culture was inoculated into 20 mL of BHI broth containing 25 $\mu$M EDDA and the culture was grown at 37° C. for approximately 3 to 4 h. Cells grown to mid-log phase ($A_{578}>0.5$) were harvested by centrifugation at 10,000×g for 20 min. The pellet was used for extraction of transferrin receptor (TfR2) protein as described in Example 3 below.

Example 2

This Example illustrates the generation of a non-clumping strain (RH408) of M. catarrhalis.

M. catarrhalis strain 4223 was inoculated into several flasks containing 20 mL of BHI broth, and the cultures were incubated with shaking (170 rpm) overnight at 37° C. Five mL of each overnight culture were transferred to individual 1 mL tubes, and were left sitting undisturbed at room temperature for 3 to 8 hours, to allow bacteria to sediment. One hundred $\mu$L of the cleared upper phase of each culture medium were used to inoculate 25 mL of BHI broth and cultures were incubated overnight at 37° C., as described above. This passaging was repeated six times, using 25 $\mu$L of cleared medium to inoculate 25 mL of BHI for each overnight culture. Non-clumping bacterial cultures were identified by measuring the $A_{578}$ at intervals over a 3 hour time period, in order to compare the sedimentation rates of the passaged strains to that of the original M. catarrhalis strain 4223 culture. Non-clumping mutants, including M. catarrhalis RH408, did not aggregate during the three hour time period. On BHI agar plates, strain RH408 had a colony morphology typical for all non-clumping strains. Strain RH408 is deposited at the American Type Culture Collection (ATCC) at 10801 University Boulevard, Manassas, Va. 20110–2209, U.S.A., under the terms of the Budapest Treaty, on Dec. 13, 1994 and was given ATCC Accession No. 55637.

Example 3

This Example illustrates the extraction of transferrin receptor protein TfR2 by affinity purification.

Affinity purified TfR2 was prepared from total membranes as described in reference 29 using Sepharose 4B (Pharmacia) conjugated human transferrin (Sigma). Bacterial receptor proteins bound to the affinity matrix were selectively eluted using a buffer of 50 mM Tris-HCl pH 8.0, 1M NaCl, 10 mM EDTA, 0.05% sodium lauryl sarkosinate, 2M guanidine. Eluted proteins were dialized against 50 mM Tris-HCl pH 8.0.

Example 4

This Example illustrates the extraction and purification of transferrin receptor protein TfR2.

Transferrin receptor protein was isolated from *M. catarrhalis* by the procedure generally illustrated in FIG. 1.

A cell pellet from iron-deprived overnight cultures of *M. catarrhalis* was resuspended in 50 mM Tris-HCl, pH 8.0, and disrupted by sonication. The sonicate was centrifuged at 20,000×g for 30 minutes and the resultant supernatant (S1), which contained soluble proteins, was discarded. The pellet (PPT1) was suspended in 50 mM Tris, pH 8.0 containing 0.5% Triton X-100 and 10 mM EDTA. This extraction step solubilized TfR2. The suspension was centrifuged at 20,000×g for 20 minutes to remove insoluble material and the supernatant was applied to a DEAE-Sephacel (Pharmacia) column equilibrated in 50 mM Tris-HCl buffer, pH 8.0. TfR2 was recovered in the flow-through fraction and was further purified using a SE-cellulose D529 column equilibrated in 50 mM Tris-HCl, pH 8.0. The flow-through fraction containing TfR2 was next loaded onto a hydroxyapatite (HTP) column equilibrated in 10 mM phosphate buffer, pH 8.0. This step separated OMP B2 (present in the HTP flow-through fraction) from TfR2 which remained bound to the HTP. After extensive washing of HTP column with 50 mM phosphate buffer, pH 8.0, TfR2 was eluted from the matrix with a 200 mM phosphate buffer, pH 8.0. The purity of TfR2 was assessed by SDS-PAGE analysis.

Example 5

This Example describes the purification of *M. catarrhalis* outer membrane protein B2 OMP B2.

The flow-through fraction of HTP column was analyzed by 12.5% SDS-PAGE. Following electrophoresis, a gel slice corresponding to the OMP B2 protein band was cut from the gel. Protein was recovered from the gel slice by electroelution for 12 hours at 100 volts in elution buffer (15mM $NH_4CO_3$/0.1% SDS).

Example 6

This Example illustrates the immunization of guinea pigs.

Guinea pigs (Charles River, Quebec) were immunized intramuscularly (i.m.) on day 1 with a 5 µg dose of either TfR2 or OMP B2 protein emulsified in complete Freund's adjuvant (CFA). Animals were boosted on days +14 and +28 with the same dose of protein emulsified in incomplete Freund's adjuvant (IFA). Blood samples were taken on day +42.

Example 7

This Example describes the analysis of purified TfR2 and OMP B2 proteins.

Proteins were separated by SDS-PAGE as described by Lugtenberg et al (ref. 36) using 11.5% or 12.5% (w/v) acrylamide (BRL) in the separating gels. Proteins were visualized by staining gels with Coomassie brilliant blue (BioRad). Protein standard molecular mass markers were from BioRad and Pharmacia.

Proteins separated by SDS-PAGE were electroblotted by the method of Towbin et al (ref. 37) onto polyvinylidene difluoride membranes (PVDF, Millipore). For immunoblots, antisera were used at dilutions of 1:1,000. Recombinant protein G horseradish peroxidase conjugate (Zymed) was used as a reporter at a dilution of 1:4,000. Blots were developed using either a olourimetric reaction (4CN/DAB; Pierce) or a chemiluminescent reaction (LumiGlo; Kirkegaard and Perry). Procedures recommended by the manufacturers were followed for both detection methods. Prestained molecular mass markers were purchased from BioRad.

In vitro transferrin-binding activity of the purified proteins was assessed following the method described by Schryvers and Lee (ref. 27) with some modifications. Briefly, protein samples were separated by SDS-PAGE and then electrophoretically transferred to PCDF membranes. The membranes were incubated with horseradish peroxidase conjugated human transferrin (1:50 dilution; Jackson ImmunoResearch) overnight at 4° C. Blots were developed using the LumiGlo chemiluminescent reaction described above.

Example 8

This Example illustrates the bactericidal assay against *B. catarrhalis*.

Samples (25 µL) of antiserum, were heated to 56° C. for 30 minutes to remove complement activity and diluted 1:8 in veronal buffer (NaCl 8.0 g/L, $NaHCO_3$ 0.25 g/L, Na Barbiturate 0.30 g/L, Barbituric acid 0.45 g/L, $MgCl_2$. $6H_2O$ 0.1 g/L, $CaCl_2.2H_2O$ 0.05 g/L) containing 0.1% BSA (VBS), and then added to the first well of a 96-well Nunc microtiter plate. Two-fold serial dilutions of antisera in VBS were placed in the remaining wells. Bacterial cells grown to an $OD_{578}$>0.5 were diluted 1:200,000 in VBS and 25-µL portions of the bacterial suspension were added to each well. A guinea pig complement (Biowhittaker, Walkersville, Md.) was diluted 1:10 in VBS and 25 µL of the solution were added to each well to initiate reactions. The plates were incubated at 37° C. for 60 min, and 50 µL of each reaction mixture was then plated onto Mueller-Hinton agar plate containing 2.2% Mueller-Hinton broth and 1.5% agar. After incubation at 37° C. for 48 hours, colonies were counted to determine the bactericidal titer (the reciprocal of the highest dilution of antiserum capable of killing greater than 50% of bacteria compared with controls containing pre-immune sera).

SUMMARY OF THE DISCLOSURE

In summary of this disclosure, the present invention provides a transferrin receptor protein having an apparent molecular mass of about 80 kDa to about 90 kDa and isolated from *M. catarrhalis*, methods of making the same and uses thereof as immunogenic compositions and diagnostic embodiments. Modifications are possible within the scope of this invention.

TABLE 1

Bactericidal activity of guinea pig antisera obtained by immunization with transferrin receptor protein (TfR2) from *M. catarrhalis* 4223

| Immunogen | Titre[1] | |
|---|---|---|
| | Pre-immune | Post-immune |
| TfR2 | <3.0 | 13.5 |
| OMP B2 | <3.0 | <3.0 |

[1]Bactericidal titres: expressed in $log_2$ as the dilution of antiserum capable of killing 50% of cells of *M. catarrhalis* 4223.

REFERENCES

1. Bluestone, C. D., *Clin. Infect. Dis.* 14 (Suppl): S197–S203 (1992)
2. Van Hare G. F., P. A. Shurin, C. D. Marchant, N. A. Cartelli, C. E. Johnson, D. Fulton, S. Carlin, and C. H. Kim. Acute otitis media caused by *Branhamella catarrahlis*: biology and therepy. Rev. Infect. Dis. 9:16–27.
3. Chapman, A. J., D. M. Musher, S. Jonsson, J. E. Clarridge, and R. J. Wallace. 1985. Development of bactericidal antibody during *Branhamella catarrhalis* infection. J. Infect. Dis. 151:878–882.
4. Hager, H., A. Verghese, S. Alvarez, and S. L. Berk. 1987. *Branhamella catarrhalis* respiratory infections. Rev. Infect. Dis. 9:1140–1149.
5. McLeod, D. T., F. Ahmad, M. J. Croughan, and M. A. Calder. 1986. Bronchopulmonary infection due to *M. catarrhalis*. Clinical features and therapeutic response. Drugs 31(Suppl.3):109–112.
6. Nicotra, B., M. Rivera, J. I. Luman, and R. J. Wallace. 1986. *Branhamella catarrhalis* as a lower respiratory tract pathogen in patients with chronic lung disease. Arch.Intern.Med. 146:890–893.
7. Ninane, G., J. Joly, and M. Kraytman. 1978. Bronchopulmonary infection due to *Branhamella catarrhalis* 11 cases assessed by transtracheal puncture. Br. Med. Jr. 1:276–278.
8. Srinivasan, G., M. J. Raff, W. C. Templeton, S. J. Givens, R. C. Graves, and J. C. Mel. 1981. *Branhamella catarrhalis* pneumonia. Report of two cases and review of the literature. Am. Rev. Respir. Dis. 123:553–555.
9. West, M., S. L. Berk, and J. K. Smith. 1982. *Branhamella catarrhalis* pneumonia. South. Med. J. 75:1021–1023.
10. Brorson, J-E., A. Axelsson, and S. E. Holm. 1976. Studies on *Branhamella catarrhalis* (*Neisseria catarrhalis*) with special reference to maxillary sinusitis. Scan. J. Infect. Dis. 8:151–155.
11. Evans, F. O., Jr., J. B. Sydnor, W. E. C. Moore, G. R. Moore, J. L. Manwaring, A. H. Brill, R. T. Jackson, S. Hanna, J. S. Skaar, L. V. Holdeman, G .S. Fitz-Hugh, M. A. Sande, and J. M. Gwaltney, Jr. 1975. Sinusitis of the maxillary antrum. N. Engl. J. Med. 293:735–739.
12. Tinkelman, D. G., and H. J. Silk. 1989. Clinical and bacteriologic features of chronic sinusitis in children. Am. J. Dis. Child. 143:938–942.
13. Wald, E. R., C. Byers, N.Guerra, M.Casselbrant, and D. Beste. 1989. Subacute sinusitis in children. J.Pediatr. 115:28–32.
14. Wald, E. R., G. J. Milmoe, A. Bowen, J.Ledesma-Medina, N. Salamon, and C. D. Bluestone. 1981. Acute maxillary sinusitis in children. N. Engl. J. Med. 304:749–754.
15. Christensen, J. J., and B. Bruun. 1985. Bacteraemia caused by a beta-lactamase producing strain of *Branhamella catarrhalis*. Acta. Pathol. Microbiol. Immunol. Scand. Sect. B 93:273–275.
16. Craig, D. B., and P. A. Wehrle. 1983. *Branhamella catarrhalis* septic arthritis. J. Rheumatol. 10:985–986.
17. Gray, L. D., R. E. Van Scoy, J. P. Anhalt, and P. K. W. Yu. 1989. Wound infection caused by *Branhamella catarrhalis*. J. Clin. Microbiol. 27:818–820.
18. Guthrie, R., K. Bakenhaster, R. Nelson, and R. Woskobnick. 1988. *Branhamella catarrhalis* sepsis: a case report and review of the literature. J. Infect. Dis. 158:907–908.
19. Hiroshi, S., E. J. Anaissie, N. Khardori, and G. P. Bodey. 1988. *Branhamella catarrhalis* septicemia in patients with leukemia. Cancer 61:2315–2317.
20. O'Neill, J. H., and P. W. Mathieson. 1987. Meningitis due to *Branhamella catarrhalis*. Aust. N. Z. J. Med. 17:241–242.
21. Morgan, M. G., McKenzie, H, Enright, M. C., Bain, M. and Emmanuel, F. X. S. (1992) Use of molecular methods to characterize *Moraxella catarrhalis* strains in a suspected outbreak of nosocomial infection. Eur. J. Clin. Microbiol. Infect. Dis. 11, 305–312.
22. Wallace, M. R., Oldfield, B. C., 1990, *Arch. Intern. Med.* 150: 1332–1334.
23. Otto, B. R., Verweij-van, Vught A. M. J. J. MacLaren, D. M. 1992, *Crit. Rev. Microbiol.* 18: 217–233
24. Schryvers, A. B. and Morris, L. J. 1988 Identification and Characterization of the transferrin receptor from *Neisseria meningitidis*. Mol. Microbiol. 2:281–288.
25. Lee, B. C., Schryvers, A. B. Specificity of the lactoferrin and transferrin receptors in *Neisseria gonorrhoeae*. Mol. Microbiol. 1988; 2–827–9.
26. Schryvers, A. B. Characterization of the human transferrin and lactoferrin receptors in *Haemophilus influenzae*. Mol. Microbiol. 1988; 2: 467–72.
27. Schryvers, A. B. and Lee, B. C. (1988) Comparative analysis of the transferrin and lactoferrin binding proteins in the family *Neisseriaceae*. Can. J. Microbiol. 35, 409–415.
28. Schryvers, A. B. and Gonzalez, G. C. 1989. Comparison of the abilities of different protein sources of iron to enhance Neisseria meningitidis infection in mice. Infect. Immun. 57:2425–2429.
29. Yu, R. and Schryvers, A. B., 1993. The interaction between human transferrin and transferrin binding protein 2 from *Moraxella* (*Branhamella*) *catarrhalis* differs from that of other human pathogens. Microbiol. Pathogenesis, 15:433–445.
30. Sethi S., Hill, S. L., Murphy, T. F. 1995, *Infect. Immun.* 63: 1516–1520
31. Helimen, M. E., Maciver, I., Latimer, J. L., Cope, L. D., McCracken, G. H and Jansen, E. J., 1993. A major outer membrane protein of *Moraxella catarrhalis* is a target for antibodies that enhance pulmonary clearance of the pathogen in an animal model. Infect. Immuno. 61, 2003–2010.
32. Campagnari, A. A., Shanks, K. L., Dyer D. W. 1994, Infect. Immun. 62: 4909–4914
33. Lockhoff, 0. Glycolipids as Immunomodulators: Synthesis and Properties. 1991. Chem. Int. Ed. Engl. 30:1611–1620.
34. Nixon-George et al (1990), J. Immunology, 144:4798–4802.
35. Sarwar, J., Campagnari, A. A., Kirkham, C. and Murphy, T. F. (1992). Characterization of an antigenically conserved heat-modifiable major outer membrane protein of *Branhamella catarrhalis*. Infect. Immun. 60, 804–809.
36. Lugtenberg, B., Meijers, J., Peters, R., van der Hoek, P. and van Alphen, L. (1975). Electrophoretic resolution of the major outer membrane proteins of *Escherichia coli* into four bands. FEBS Lett. 58, 254–258.
37. Towbin H., Staehelin, T., Gordon, J. 1979, *Proc. Natl. Acad. Sci.* 76: 4350–4354.

What we claim is:

1. An isolated and purified non-denatured transferrin receptor protein of a strain of *Moraxella catarrhalis* having an apparent molecular mass of about 80 to about 90 kDa, as determined by sodium dodecyl sulphate polyacrylamide gel electrophoresis (SDS-PAGE).

2. The protein of claim 1 wherein the strain is *Moraxella catarrhalis* 4223, 5191 or 135.

3. The protein of claim 1 which is at least about 70 wt % pure.

4. The protein of claim 3 which is at least about 90 wt % pure.

5. A composition, comprising an aqueous solution of an isolated and purified non-denatured transferrin receptor protein of a *Moraxella catarrhalis* strain having an apparent molecular mass of about 80 to about 90 kDa, as determined by sodium dodcecyl sulphate polacrylamide gel electrophoresis (SDS-PAGE).

6. The protein of claim 1 free from the OMP B2 protein of the *Moraxella catarrhalis* strain.

7. The protein of claim 1 free from the transferrin receptor protein of the *Moraxella catarrhalis* strain having an apparent molecular mass of about 105 kDa.

* * * * *